United States Patent [19]

Dodick et al.

[11] Patent Number: 5,906,611
[45] Date of Patent: May 25, 1999

[54] SURGICAL INSTRUMENT WITH LASER TARGET

[76] Inventors: Jack Murray Dodick, 535 Park Ave., New York, N.Y. 10021; Reinhardt Thyzel, Seestrasse 9, 8640 Rapperswil, Sweden

[21] Appl. No.: 08/901,302

[22] Filed: Jul. 28, 1997

[51] Int. Cl.[6] .................................................. A61B 17/36
[52] U.S. Cl. .................................. 606/16; 606/13; 606/6; 606/2
[58] Field of Search ..................... 606/2, 2.5, 4, 5, 606/6, 13–16; 601/2

[56] References Cited

U.S. PATENT DOCUMENTS

| | | |
|---|---|---|
| 3,982,541 | 9/1976 | L'Esperance Jr. . |
| 3,993,064 | 11/1976 | McCarthy et al. . |
| 4,045,630 | 8/1977 | McCarthy et al. . |
| 4,052,985 | 10/1977 | Coleman et al. . |
| 4,207,874 | 6/1980 | Choy . |
| 4,377,897 | 3/1983 | Eichenbaum et al. . |
| 4,386,927 | 6/1983 | Eichenbaum . |
| 4,538,608 | 9/1985 | L'Esperance Jr. . |
| 4,538,611 | 9/1985 | Kelman . |
| 4,551,129 | 11/1985 | Coleman et al. . |
| 4,559,942 | 12/1985 | Eisenberg . |
| 4,573,467 | 3/1986 | Rich et al. . |
| 4,583,539 | 4/1986 | Karlin et al. . |
| 4,597,388 | 7/1986 | Koziol et al. . |
| 4,638,801 | 1/1987 | Daly et al. . |
| 4,694,828 | 9/1987 | Eichenbaum . |
| 5,041,121 | 8/1991 | Wondrazek et al. . |
| 5,057,098 | 10/1991 | Zelman ........................................ 606/6 |
| 5,224,942 | 7/1993 | Beuchat et al. ........................... 606/2.5 |
| 5,324,282 | 6/1994 | Dodick . |
| 5,425,735 | 6/1995 | Rosen et al. ............................... 606/2.5 |
| 5,738,677 | 4/1998 | Colvard et al. .............................. 606/4 |

FOREIGN PATENT DOCUMENTS

| | | |
|---|---|---|
| 8804540 | 6/1988 | European Pat. Off. . |
| 3842916 | 2/1990 | Germany . |

*Primary Examiner*—John P. Leubecker
*Assistant Examiner*—Bryan K. Yarnell
*Attorney, Agent, or Firm*—McAulay Nissen Goldberg Kiel & Hand, LLP

[57] ABSTRACT

A surgical needle with an open distal port at which tissue to be fractured is positioned contains an optical fiber for providing pulses of laser energy and a titanium target that receives these pulses. The target converts the energy in the electromagnetic pulses to shockwaves that impinge on the tissue at the port causing the tissue to fracture. The target has one or more steps such that vaporization of the target by the laser pulses leaves a surface which directly faces the port so that the continued conversion of laser energy to mechanical shockwaves will provide shockwaves that are not blocked in traveling to the port at which the tissue is located.

7 Claims, 3 Drawing Sheets

SURGICAL INSTRUMENT WITH LASER TARGET

BACKGROUND OF THE INVENTION

This invention relates to a laser powered surgical instrument that employs a target for transducing laser energy into shockwaves.

The particular application of this invention is to a surgical instrument used in eye surgery and particularly for cataract removal. However, the invention may be embodied in devices which are adapted to other surgical procedures.

The use of laser energy to perform eye surgery is well known. In particular, the use of laser energy to impinge on a metal target so as to cause optical breakdown to generate shockwaves is known in applicant's U.S. Pat. No. 5,324,282. The patent discusses some of the background of the art.

More particularly, the patent discloses a design of the distal end of a surgical needle that is used for breaking up cataracts. The arrangement is one where laser pulses impinge on a target at the distal end of the needle to generate shockwaves that travel to a port of the needle at which the tissue to be fractured is positioned.

As discussed in the '282 Patent, there are a number of desirable goals for a laser operated surgical device including efficiency of operation to minimize weight, cost and size as well as to minimize heat generated and to assure maximum effect. One of the important goals is to have a minimum size diameter for the surgical instrument or the needle involved so that only a small incision need be made in the patient's eye thereby minimizing trauma and enhancing recovery. As stated in the '282 Patent, safety, comfort and minimum trauma consistent with performing the operation is the goal of the surgical instruments.

One of the instruments disclosed in the '282 Patent is disclosed herein as prior art in FIG. 5. As shown in FIG. 5, a surgical needle 50 having an O.D. of about 2.0 mm has a sidewall 52 containing an evacuating passageway 54 and an optical fiber 56 to provide pulses of laser energy. The pulses of laser energy, in one embodiment, are provided by a neodymium-YAG laser that provides light energy at a wavelength of 1,064 nano-meters. It is delivered in pulses having a width of approximately 8 nano-seconds. These pulses impinge on a target wall 58 to cause breakdown of the target and generation of plasma at the target which causes shockwaves to be transmitted to the port 60.

What has been found is that the laser pulses develop a pit in the target 58. The pit then tends to capture some of the shockwaves generated and make the application of the energy to the tissue less efficient.

In addition, particles of the vaporized target get in the path of the laser pulses thereby reducing the level of laser energy that impinges on the target and thus making the operation of the instrument less efficient.

Accordingly, a major purpose of this invention is to provide an improved surgical instrument design using the laser transducer function in which the instrument operates more effectively and efficiently and specifically to provide shockwaves that are greater in intensity at the tissue to be fractured.

BRIEF DESCRIPTION OF THE INVENTION

In brief, one embodiment of this invention involves a surgical needle in which a laser fiber extends the length of the needle and terminates near the distal end of the needle. The rest of the interior of the needle may be used to provide a flow of saline fluid to the distal end of the needle or, alternatively, to aspirate saline and tissue particles from the distal end of the needle.

At the distal end of the needle, there is a port which is held against the cataract tissue to be fractured. In addition, at the distal end of the needle there is a stepped titanium metal target which is spaced from the distal end of the laser fiber to receive pulses of laser energy. The resultant optical breakdown at the target produces shockwaves that impinge upon the tissue at the port and thereby fracture the tissue.

The stepped titanium target has a first wall surface that is perpendicular to the axis of the needle and which is spaced a first predetermined distance from the distal end of the laser fiber. A second target wall, which is also a surface perpendicular to the axis of the needle, is spaced a somewhat greater predetermined distance from the distal end of the needle. These two walls are connected by a step which is the surface substantially parallel to the longitudinal axis of the needle. The step is closely aligned with the axis of the laser fiber so that the laser pules are received on both the first and second walls. As the pulses impinge on the target, a portion of the first wall adjacent to the step vaporizes and a groove is created that extends distally toward the second wall. Because the zone of the target that vaporizes is along the step, the shockwaves are in direct communication with the port and are not blocked by any portion of the target.

Concurrently, a certain portion of the second wall vaporizes to provide additional shockwaves and enhance the effect of the vaporization from ablation of the first wall. Accordingly, since the ablation of the target occurs along the longitudinal surface that is the step, the shockwaves generated from the interaction of the laser pulses with the target material are emitted from a surface of the target so as to impinge on the tissue at the port of the surgical needle.

BRIEF DESCRIPTION OF THE FIGURES

FIG. 1 illustrates the offset within the surgical instrument of the optical fiber that carries the pulses of laser energy.

FIG. 1 is a longitudinal cross-section through the axis of the needle and the axis of the laser fiber.

DESCRIPTION OF THE PREFERRED EMBODIMENTS

Figure 1:
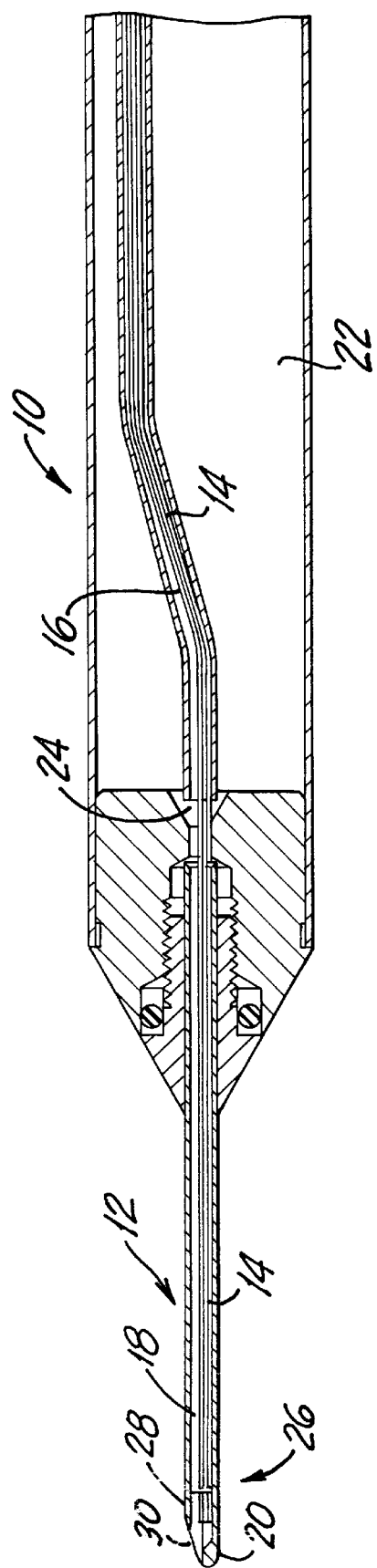
FIG. 1 is a longitudinal sectional view through a first embodiment of this invention illustrating the needle and the handpiece which holds the needle.

As shown in FIG. 1, a handpiece 10 holds the surgical needle 12. An optical fiber 14 designed to carry the desired laser pulses extends through an inner passageway 16 in the handpiece 10 and through a passageway 18 in the needle 12. The bend in the passageway 16 causes the laser fiber 14 to be positioned, as shown, along a predetermined portion of the wall of the passageway 18 in the needle. As may best be seen in FIG. 2, this technique provides for appropriately positioning the laser fiber 14 relative to the target 20.

The outer passageway 22 in the handle can be used to provide for infusion of saline into the passageway 18 of the needle or for aspiration of saline and tissue from the needle passageway 18 through the passageways 18 and 22. As can be seen at the communication zone 24, the coupling between the handpiece 10 and needle 12 provides for such communication.

Figure 2:
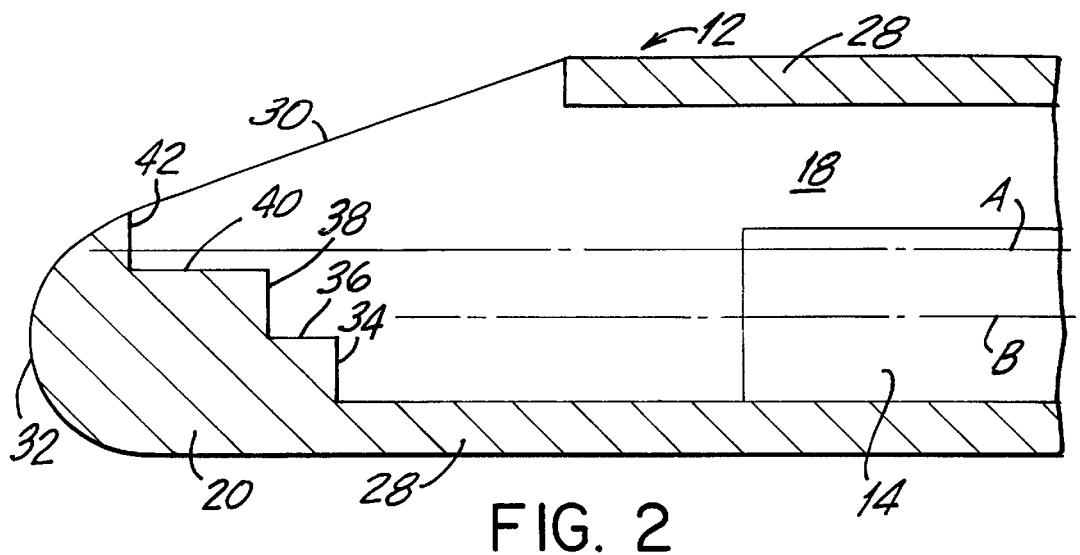
FIG. 2 is a longitudinal section of the distal end of the FIG. 1 instrument. In particular.

FIG. 2 is a longitudinal section of the distal portion of the needle 12 illustrating the particular target 20 arrangement. In one embodiment, the distal cannula segment 26 has an outside diameter (O.D.) of 1.200 millimeters (mm) and an inside diameter (I.D.) of 0.90 mm. Accordingly, the sidewall 28 has a thickness of 0.15 mm. This distal segment 12 is made of titanium so that the target 20 will be of the desired titanium material. The distal segment 12 is mounted on a stainless steel segment of the needle 12. Because of the way the optical fiber 14 is mounted along the passageway 16 in the handle 10, it lies against the side of the wall of the needle as shown so that the fiber 14 is appropriately positioned relative to the target 20.

In this embodiment, the plane of the port 30 has an angle of 19° to the centerline of the passageway 16. The port 30 extends from a point that is approximately 0.30 mm from the nose 32 to a point which is approximately 1.60 mm from the nose 32. The centerline B of the fiber 14 is offset from the centerline A of the needle 12 so that the distal end of the fiber 14 is in alignment with the target 20.

Most important is the design and positioning of the target 20. The target has a first wall 34, a first step 36 and a second wall 38. A second step 40 leads to an end wall 42. The first wall 34 is 0.20 mm at its highest. The step 36 is 0.20 mm. The second wall 38 is 0.20 mm. The second step 40 is 0.40 mm. Since the fiber 14 has an O.D. of 0.47 mm and a core 0.40 mm, the centerline of the laser fiber 22 is close to the first step 36. As a consequence, substantially the center of the laser beam impinges on the target 20 at approximately the zone of the first step 36.

Figure 3:
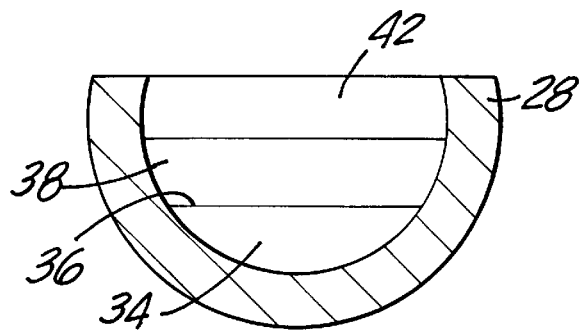
FIG. 3 is a cross-sectional view along the plane 3—3 of FIG. 2.
Figure 5:
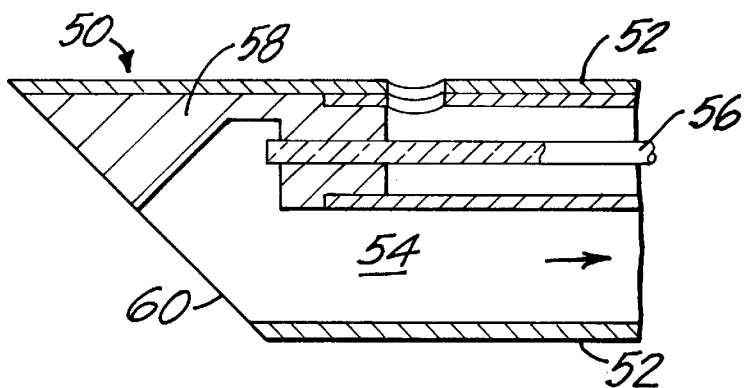
FIG. 5 is an illustration of one of the prior art devices shown in U.S. Pat. No. 5,324,282 and in particular is an illustration of the device shown in FIG. 5 of that patent.

The needle is circular in cross-section. Thus the first wall 34 has a variable height. The 0.20 mm dimension recited above is for the line at the longitudinal cross-section through the needle axis and laser fiber axis. FIG. 3 provides a view of the two walls.

Although the laser fiber 14 can be positioned at various distances from the wall 34, it is presently preferred to position it 1.2 mm from the target wall 34. It might be noted that when the distance is much less than 1.2 mm, the shockwaves generated are stronger. But there is a tenancy to destroy the fiber. If the fiber 14 is positioned further away than 1.2 mm, the magnitude of the shockwaves is reduced.

In terms of analysis of what happens, it helps to keep in mind that there is a slightly diverging beam with an angle of perhaps 4° and, more importantly, there is a concentration of energy at the centerline of the laser beam with a substantial drop off toward the edges of the laser beam.

What happens in an operation is that the center part of the laser beam impinges on the upper portion of the first target wall 34. Because of the proximity between the first target wall 34 and the laser beam, the upper portion of the target wall 34 vaporizes most rapidly. However, the second target wall 38 also vaporizes because of the laser beam although it does so at a slower rate. As a consequence, during the operation, the step 36 is largely removed. The step 40 which is in alignment with a portion of the laser beam is not entirely destroyed. What is important is that because of the first step 36, as the target wall 34 vaporizes, the shockwaves are directly received at the port 30. By the time the step 36 is vaporized, some of the second target wall 38 has also been vaporized so that a portion of the target 20 defined by the wall 38 and step 40 will also produce shockwaves that are received at the port 30. However, by the time any substantial amount of the wall 38 has been vaporized, a sufficient number of shockwaves will have been produced to complete the operation.

A neodymium-YAG laser that provides eight (8) nano-second wide pulses of 1,064 nano-meter laser light has been successfully used. In one such embodiment, 900 pulses or shots can be generated before a pit is bored into the target at the wall 38, which pit tends to block and deflect the shockwaves. It is of some interest to note that about 2,800 shots or pulses will puncture a hole all the way through the target 20 to the nose 32.

These pulses can be provided at a repetition rate of anywhere between two and fifty pulses per second and anywhere between two and fifteen milli-joules of energy per pulse. Applicant prefers a pulse duration of between 8 and 12 nano-seconds. At present, applicant prefers a repetition rate of between two and six pulses per second and an energy per pulse of between six and ten milli-joules. Under those conditions between 200 and 800 pulses or shots will be effective to handle most cataract operations.

Accordingly, the design shown overcomes the limitation of the target design shown in the referenced patent by avoiding the creation of a pit in the target until after a sufficient number of shock pules have been generated and received at the port 24 to accomplish the desired operation.

As mentioned above, the passageway 18 can be used for either aspiration or infusion. If used for aspiration, then a separate infusion needle will be required for the operation in a cataract application. One advantage of having the dual needle arrangement is that it permits a smaller size needle for the same capacity than does the prior art design shown in FIG. 4. The smaller size needle can have a 1.2 mm or less outside diameter (OD). The cooperating infusion needle would have an OD of substantially less than the OD of the needle 12. The smaller incisions will result in more rapid healing of the incision as well as reducing the likelihood of induced a stigmatism. A further advantage of the smaller diameter needle is that there can be better control over leakage out of the incision during operation because of the smaller size of the incision required to accommodate the needle.

It is possible to use the target design of this invention in a needle that includes both aspiration and infusion. Such is not presently preferred for the following reasons. One reason, as indicated above, is that separating the aspiration and infusion functions into two separate needles reduces the size of the incision required with the consequent advantages mentioned above. A second reason is where there is a positive flow through the port 30 either into the passageway 18 (where the passageway 18 is used for aspiration) or out of the passageway 18 (where the passageway 18 is used for infusion), the zone between the end of the fiber and the target 34, 38 tends to be cleared of particles. Applicant believes these particles are primarily atomic or molecular size titanium particles. Clearing the particles assures that the maximum amount of laser energy impinges on the target. Experiments have shown that the flow of fluid through the port 30 increases the net energy produced by each laser pulse on the target.

Figure 4:
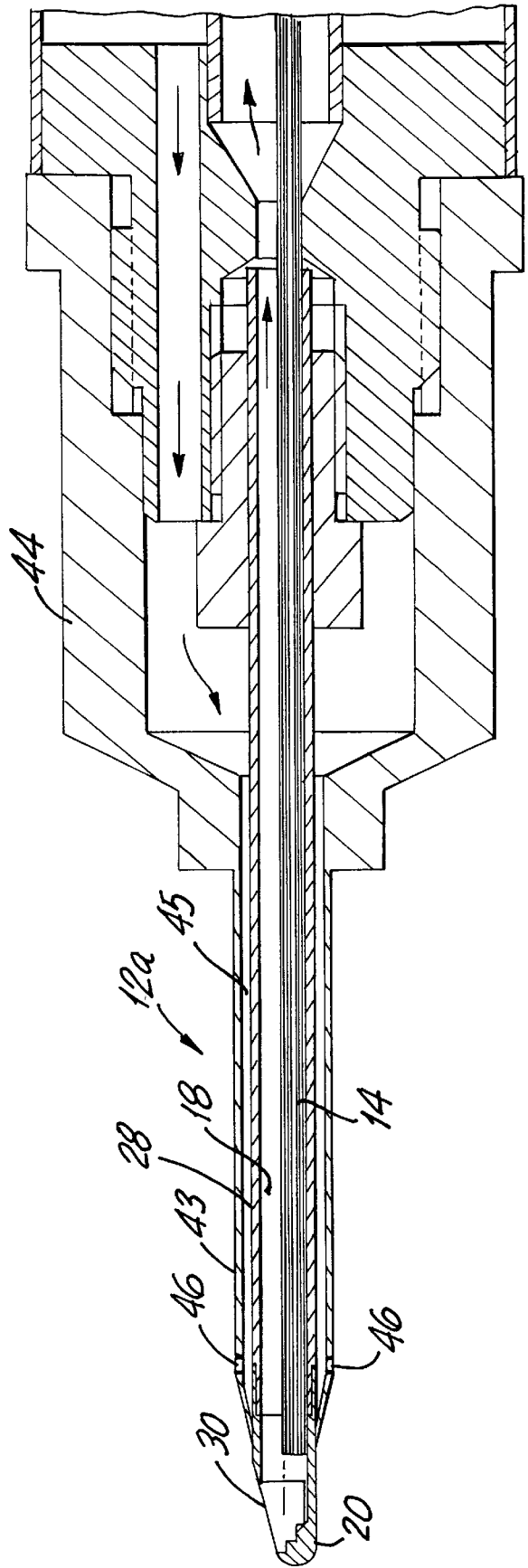
FIG. 4 is a longitudinal sectional view of a second embodiment of the invention in which both aspiration and infusion are provided by the needle having the laser fiber.

However, there may be circumstances where a single instrument design is preferable. FIG. 4 shows a uni-manual embodiment of the invention in which the stepped target arrangement is incorporated in a needle that contains both aspiration and infusion. The reference numbers for parts similar to those in the FIG. 1–3 embodiment are carried over into the FIG. 4 embodiment for ease of comparison.

The optical fiber 14 for carrying the laser energy is deployed in the FIG. 4 embodiment in the same fashion as in the FIG. 1 embodiment. However, the needle 12A is somewhat different in that it has a tubular sheath 43. The sheath 43 is the distal portion of a removable plastic snap on element 44. The sheath 43 creates an annular passageway 45 which in this embodiment is used for the infusion of saline. With the sheath 43 inserted over the needle 12, the needle 12A OD is approximately 2.1 mm. The sheath 43 has two radial ports 46 and is closed at its distal end. Through ports 46, saline exits to flow into the area of the operation and to flow back through the port 30 and out through the aspirating passageway 18.

In FIG. 4, arrows show the direction of flow. It should be noted that the plastic snap-on member 44 could well be a permanent metal member. Whether or not the member 44, together with the sheath 43, is removable or not will depend upon whether or not it is desirable to have separate instruments for a uni-manual instrument as shown in FIG. 4 and for a bi-manual instrument as shown in FIG. 1. The target 20 in the FIG. 4 embodiment is the same as the target 20 in the FIG. 1 embodiment.

In one version of the FIG. 4 embodiment, the two 180° spaced apart ports 46 have a diameter of 0.6mm.

Some surgeons may prefer a single needle arrangement in which both aspiration and infusion are in the laser delivery needle. A single needle design facilities a one hand operation and also means there is only a single incision. There is a trade-off of advantages and disadvantages between the FIG. 1 and FIG. 4 designs; the selection of which will be a function of individual choice and judgement.

Although the invention has been described in connection with particular embodiments, it should be understood there are variations in the embodiment which are incorporated within the inventive concept claimed.

For example, the presently preferred two step target could be replaced by a single step target which might be simpler to manufacture and which, depending upon the application, might provide a sufficient number of pulses to complete the operation involved.

It is within the skill of those in this art to effect an appropriate trade-off of target size, target position, number of pulses required for a particular operation and the power delivered by each laser pulse.

What is claimed is:

1. In a surgical needle for fracturing tissue at an operating port through the generation of shockwaves due to plasma formation from the optical breakdown of a target on which laser pulses from a laser beam impinges, the improvement comprising:

said target having a first target wall, a first step and a second wall, said first step extending between said first and second walls, a laser fiber having a centerline spaced from said first target wall at a predetermined distance, said centerline of said laser fiber being in alignment with a predetermined zone around said first step to assure vaporization of a substantial portion of said first step when said target is hit with laser pulses from said fiber, whereby there is a clear line of sight between the shockwaves generated and the operating port.

2. The improvement of claim 1 wherein:

said second wall is a target wall and further comprising:

a second step and an end wall, said second step extending between said second target wall and said end wall, a portion of whatever laser pulses are provided by said laser fiber impinging on said second target wall.

3. A surgical needle for fracturing tissue comprising:

a tubular sidewall having a longitudinal axis and a distal end portion, a laser fiber extending longitudinally to said distal end portion of said sidewall, said laser fiber having a centerline and a distal end, a target mounted adjacent to said distal end of said laser fiber, said target having a first target wall, a first step and a second wall, said first step extending between said first and second walls, said distal end of said laser fiber being spaced from said first target wall by a predetermined distance, said centerline of said laser fiber being in alignment with a predetermined zone around said first step to assure vaporization of a substantial portion of said first step when said target is hit with laser pulses from said fiber, a tissue receiving port at said distal end of said needle, an uninterrupted path between said first step and said tissue receiving port, breakdown of said target by laser pulses from said fiber producing shockwaves that are propagated to said tissue receiving port along said uninterrupted path.

4. The surgical needle of claim 3 further comprising:

a longitudinal passageway within said tubular sidewall extending longitudinally through said surgical needle, a distal extension of said passageway intercepting said tissue receiving port.

5. The surgical needle of claim 4 wherein:

of said tissue receiving port having a plane that is at an acute angle, less than 45°, to the longitudinal axis of said tubular sidewall.

6. The surgical needle of claim 4 further comprising:

a tubular sleeve surrounding said tubular sidewall to provide an annular passageway between said sidewall and said sleeve, said sleeve having a distal end that extends to the distal portion of said sidewall, a least one infusion port in said sleeve at said distal portion of said sidewall, said annular passageway between said sidewall and said sleeve providing an infusion passageway, and said longitudinal passageway within said sidewall providing an aspirating passageway.

7. The surgical needle of claim 3 wherein:

said tissue receiving port having a plane that is at an acute angle, less than 45°, to the longitudinal axis of said tubular sidewall.

* * * * *

UNITED STATES PATENT AND TRADEMARK OFFICE
CERTIFICATE OF CORRECTION

PATENT NO. : 5,906,611
DATED : May 25, 1999
INVENTOR(S) : Jack Murray Dodick
Reinhardt Thyzel It is certified that error appears in the above-identified patent and that said Letters Patent is hereby corrected as shown below:

Title page, item [76} inventor, Reinhardt Thyzel's address is incorrectly listed as Rapperswil, Sweden. It should read Rapperswil, Switzerland.

Signed and Sealed this

Fourth Day of April, 2000

Attest:

Attesting Officer

Q. TODD DICKINSON

Director of Patents and Trademarks